US008287552B2

(12) United States Patent
Grillo

(10) Patent No.: US 8,287,552 B2
(45) Date of Patent: Oct. 16, 2012

(54) VACUUM DEVICE FOR SEALING AN ANATOMICAL OPENING

(75) Inventor: Francis P. Grillo, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 664 days.

(21) Appl. No.: 11/083,763

(22) Filed: Mar. 18, 2005

(65) Prior Publication Data

US 2006/0212043 A1   Sep. 21, 2006

(51) Int. Cl.
*A61B 17/42* (2006.01)
*A61B 17/46* (2006.01)
*A61D 1/10* (2006.01)

(52) U.S. Cl. ...................................... 606/119; 606/123

(58) Field of Classification Search .................. 600/562, 600/563, 565, 581, 587, 591, 156; 606/119, 606/123; 604/264, 275, 278, 279, 176
See application file for complete search history.

(56) References Cited

U.S. PATENT DOCUMENTS

| | | | |
|---|---|---|---|
| 3,517,665 A | | 6/1970 | Sheldon |
| 3,777,743 A | * | 12/1973 | Binard et al. ................. 600/562 |
| 4,340,066 A | * | 7/1982 | Shah ............................. 600/562 |
| 4,534,362 A | * | 8/1985 | Schumacher et al. ........ 600/551 |
| 4,781,699 A | * | 11/1988 | Suzuki et al. ................. 604/218 |
| 5,104,377 A | | 4/1992 | Levine et al. |
| 5,259,836 A | * | 11/1993 | Thurmond et al. ........... 600/431 |
| 5,409,012 A | * | 4/1995 | Sahatjian ...................... 600/562 |
| 5,540,658 A | * | 7/1996 | Evans et al. .............. 604/101.04 |
| 2003/0171664 A1 | * | 9/2003 | Wendlandt ..................... 600/407 |
| 2004/0138526 A1 | * | 7/2004 | Guenst .......................... 600/114 |
| 2005/0085695 A1 | * | 4/2005 | Shener et al. ................. 600/156 |
| 2005/0113852 A1 | * | 5/2005 | Burbank et al. .............. 606/158 |

FOREIGN PATENT DOCUMENTS

| | | |
|---|---|---|
| DE | 4120018 | 12/1992 |
| WO | 96/38197 | 12/1996 |
| WO | 2004/082486 | 9/2004 |

* cited by examiner

*Primary Examiner* — Max Hindenburg
*Assistant Examiner* — H. Q. Nguyen
(74) *Attorney, Agent, or Firm* — Fay Kaplun & Marcin, LLP

(57) ABSTRACT

A device for accessing a hollow organ comprises an elongated body sized for insertion into an entrance passage to the hollow organ, the elongated body including an outer sealing surface engaging an inner surface of the entrance passage and a working channel extending therethrough from a proximal port which, when the elongated body is in the operative position is proximal to a proximal opening of the entrance passage, to a distal port which, when the elongated body is in the operative position, extends distally past a distal opening of the entrance passage into the hollow organ and a plurality of suction holes formed through an outer wall of the elongated body, disposed around a circumference of a portion of the elongated body which, when the elongated body is in the operative position, is located within the entrance passage in combination with a vacuum channel formed in the elongated body for transferring a negative pressure to the suction holes to increase a sealing force applied by tissue of the entrance passage to the outer surface of the elongated body.

1 Claim, 2 Drawing Sheets

VACUUM DEVICE FOR SEALING AN ANATOMICAL OPENING

BACKGROUND

A number of diagnostic and therapeutic procedures require introduction of surgical instruments into the uterus. Some of the procedures involve dilation of the cervix, to facilitate the introduction of the instruments therethrough to the uterus. However, if the cervix is over dilated or patulated or, when a device accessing the uterus is manipulated during a procedure, fluid or gas may leak from the uterus through the cervix. One type of procedure, ablation of uterine tissue to treat endometriosis (e.g., procedures using the Hydro-ThermAblator® (HTA)), may involve the application of intracavity pressure during the introduction of fluids into the uterus.

The treatment of tissue masses (e.g., fibroids and tumors) often involves ablation. For example, a tissue mass may be ablated by inserting a therapeutic device thereinto to apply electrical (RF) energy may to the tissue mass via one or more electrodes or by injecting fluids with appropriate properties into the vicinity of the tissue mass. Tissue masses within the uterus are often treated in this manner, with surgical instruments necessary to carry out the procedure being inserted into the uterus via the cervical canal.

Where the heated or caustic fluids are applied (e.g., to ablate the endometrium), the escape of such fluids from the uterus may damage non-targeted tissues. Although the cervical muscle is strong and effectively creates a seal at the opening of the uterus, procedures such as these may require mechanically enhancing the seal of the cervix around the surgical instruments, to prevent fluid or gas leakage therefrom. Mechanical enhancement of the cervix' seal may also be required where the instruments to be inserted through the cervix require extensive dilation, where the cervix is weak or where significant stresses are exerted against the cervix by movement of the surgical instruments, etc.

The cervix is often sealed during conventional procedures by clamping a tenaculum externally therearound, by wrapping suture loops therearound or by purse string suturing woven in and out of the cervix and drawn tightly to apply compression. Conventional tenaculums include scissor-like clamps that generate significant compression around portions of the cervix. However, multiple clamps may be required to effectively seal the cervix around its entire circumference, and suture loops are not suitable for all patients, as they often require a substantial protrusion of the cervix to enable the loop to lasso therearound. Clamps placed externally to the cervix may also increase trauma and patient discomfort.

SUMMARY OF THE INVENTION

The present invention is directed to a device for accessing a hollow organ comprising an elongated body sized for insertion into an entrance passage to the hollow organ, the elongated body including an outer sealing surface engaging an inner surface of the entrance passage and a working channel extending therethrough from a proximal port which, when the elongated body is in the operative position is proximal to a proximal opening of the entrance passage, to a distal port which, when the elongated body is in the operative position, extends distally past a distal opening of the entrance passage into the hollow organ and a plurality of suction holes formed through an outer wall of the elongated body, disposed around a circumference of a portion of the elongated body which, when the elongated body is in the operative position, is located within the entrance passage in combination with a vacuum channel formed in the elongated body for transferring a negative pressure to the suction holes to increase a sealing force applied by tissue of the entrance passage to the outer surface of the elongated body.

DETAILED DESCRIPTION

Figure 1:
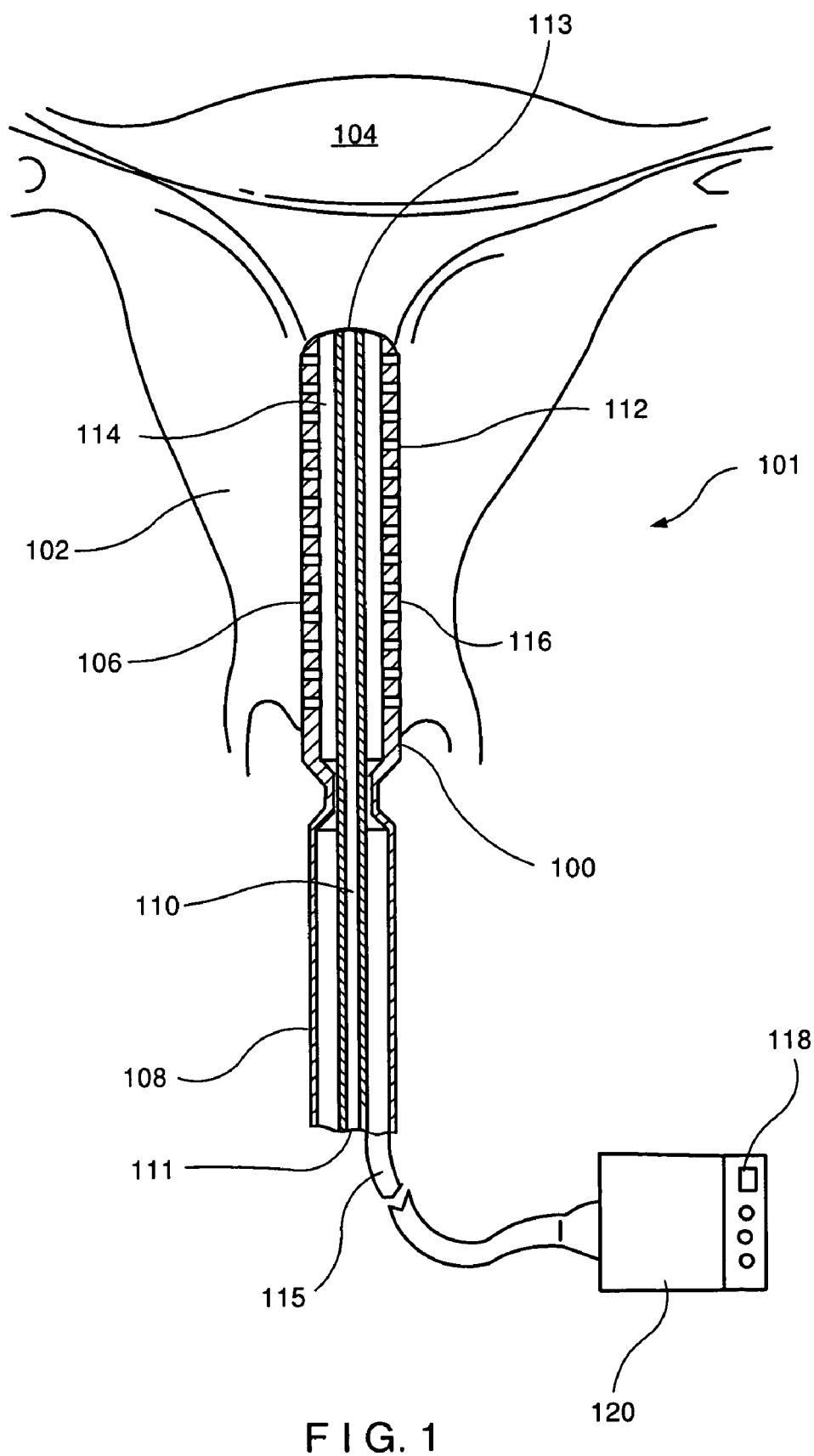
FIG. 1 is a diagram showing a first embodiment of a cervical sealing device according to the invention.

The present invention may be further understood with reference to the following description and the appended drawings, wherein like elements are referred to with the same reference numerals. The present invention is related to medical devices used to access the interior of hollow organs (e.g., the uterus) through a natural opening for medical treatment. In particular, the present invention relates to devices for reinforcing a fluid tight seal formed by a natural opening to the hollow organ (e.g., the cervix) around a medical instrument introduced into the organ therethrough.

There are a wide variety of procedures carried out wherein it is desirable to maintain a fluid tight seal around an instrument inserted into an opening of a hollow organ (e.g., in the gastrointestinal tract). Such a seal may be useful in any case where the seal provided by a natural sphincter, by a restriction or by a passage into the cavity is not sufficient to provide a fluid-tight seal when a therapeutic device is inserted therethrough. Although the following description is principally directed to a cervical sealing device used in conjunction with uterine procedures, those of skill in the art will understand that such description is illustrative only and that embodiments of the device may be used in procedures performed on a variety of other organs.

A system to perform therapeutic procedures within a hollow organ, according to an exemplary embodiment of the present invention, includes a seal member comprising an elongated body adapted for insertion through the opening of the hollow organ (e.g., the cervix) and a plurality of elements associated with the elongated body to maintain a fluid-tight seal around the elongated body. The elongated body preferably also includes a working channel extending therethrough, to permit therapeutic fluids and/or instruments to be inserted into the hollow organ therethrough.

FIG. 1 shows an exemplary embodiment of a uterine access system 101 according to the invention. The system 101 comprises a sealing member 100 sized, shaped and otherwise adapted for trans-cervical placement (i.e., through the cervix 102 to the opening of the uterus 104). The sealing member 100 forms a part of an elongated body 106 which, when the elongated body 106 is in a desired operative position, extends within an opening to a hollow organ (e.g., the cervix 102) so that a distal end 114 of the elongated body 106 opens into the hollow organ (e.g., the uterus 104) while a proximal part of the elongated body 106 extends proximally out of the opening to serve as a control portion manipulable by an operating professional.

According to embodiments fo the present invention, the seal between the sealing member 100 and the walls of the cervical canal 102 is enhanced by applying a vacuum between an outer surface of the sealing member 100 and the surrounding tissue to draw the surrounding tissue into close contact with the outer surface of the sealing member 100. The natural seal formed as the muscles of the cervix 102 contract around the elongated body 106 is supplemented as the vacuum pressure draws the tissue of the cervix 102 more tightly around the sealing member 100. As described above, the means employed in the apparatus and method of the present invention to draw the surrounding tissue into close contact with an elongated body (e.g., application of a vacuum) may be applied to any opening to a hollow organ and the following description related in particular to a transcervical device is simply exemplary.

In this embodiment, the proximal part of the elongated body 106 is formed as a shaft 108 which may be manipulated to position the elongated body 106 and its associated elements within the cervix 102. A working channel 110 extends longitudinally within the elongated body 106 between a proximal opening 111 which, when the sealing member 100 is in its operative position, remains outside the body, and a distal opening 113 which, when in the operative position, opens into the uterus 104. The working channel 110 preferably extends substantially along a longitudinal axis of the sealing member 100, to provide a passage into the uterus 104. For example, medical instruments and therapeutic devices may be inserted into the uterus 104 through the working channel 110 while the cervix remains tightly closed around the sealing member 100. In a specific exemplary embodiment, devices for carrying out endometrial ablation (e.g., using heated saline solution or other ablating fluids) may be inserted though the working channel 110 and into the uterus 104.

As shown in FIG. 1, a plurality of suction holes 112 are formed through an outer surface the sealing member 100 of the elongated body 106. The suction holes 112 are in communication with a vacuum channel 114 which extends along the length of the elongated body 106 to a proximal opening for coupling to a source of vacuum pressure. For example, the vacuum channel 114 may be formed in a wall of the distal portion of the elongated body 106, such as the wall 116 of the sealing member 100. The vacuum channel 114 may be a discrete lumen extending longitudinally along a length of the elongated body 106 or an annular gap formed in the elongated body 106 in, for example, the space found between the working channel 110 and the wall 116.

The suction holes 112 may be connected to a source of vacuum 120, for example via a vacuum line 115 which leads from the vacuum channel 114 to the source 120. The vacuum line 115 may comprise portions within the shaft 108, or may be substantially external to the elongated body 106. As would be understood by those skilled in the art, the source 120 may be any conventional vacuum or suction source, including the suction lines commonly found in medical facilities. A controller 118 may also be used with the source of suction 120 to turn the suction on and off and to select a desired level of suction. For example, the controller 118 may automatically turn the suction on during specific portions of the therapeutic procedure (e.g., when a supply of hot or caustic fluid is activated). At other times, the suction may be kept off. Alternatively, the suction may be kept on at all times while the elongated body 106 is inserted into the opening to the hollow organ. Alternatively, the suction may be manually controlled by the operating professional.

As shown in the exemplary embodiment of FIG. 1, the suction holes 112 may be placed along the entire length of the sealing member 100. However, other configurations of the suction holes 112 may be used. For example, the holes 112 may be grouped in one or more narrow circumferential bands formed around the sealing member 100, so that hollow organs with openings of various lengths can be accommodated. Various patterns and configurations of the suction holes 112 may be employed, as necessary in view of the anatomy of the opening and of the organ being treated and the opening thereto. It may be preferred to located the suction holes 112 only on those portions of the elongated body 106 where, they will be in close contact with surrounding tissue when the elongated body 106 is in the operative position. For example, as in the embodiment described above, the holes 112 may be located only along the sealing member 100 which, when in the operative position, extends within the cervix 102. If some of the holes 112 are located in positions where they cannot draw in surrounding tissue, a vacuum leak will exist weakening the seal. In another exemplary embodiment, the suction holes 112 may be formed as slots aligned in any convenient direction which maximizes the strength of the seal formed thereby.

Figure 2:
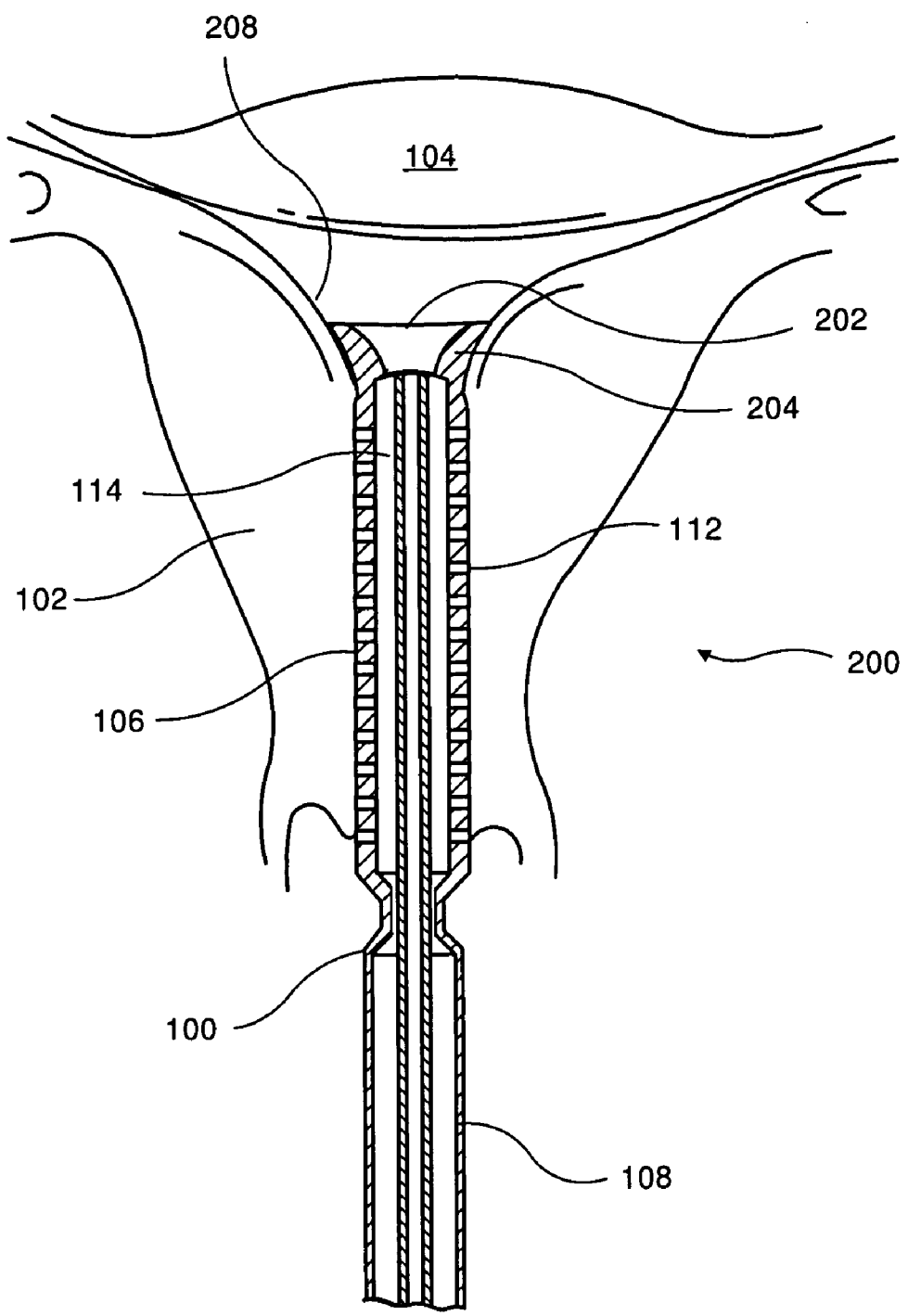
FIG. 2 is a diagram showing a second embodiment of a cervical sealing device according to the invention.

FIG. 2 shows a vacuum sealing system 200 according to a second embodiment of the present invention. This system 200 is similar to the system 100 except that, in the exemplary system 200, a tapered section 202 shaped, for example, as a cup or cone is provided at the distal end of the sealing member 100, to provide additional sealing force to uterine tissue adjacent to the opening of the cervix 102 into the uterus 104. The diameter of the tapered section 202 increases toward a distal end thereof to conform to the increasing diameter of the opening as the opening transitions to the hollow organ. Thus, those skilled in the art will understand that any shape tapered section 202 may be employed so long as the shape mirrors that of the anatomy at the opening. In this embodiment, the tapered section 202 is designed to fit tightly onto the opening 208 from the cervix 102 into the uterus 104. The tapered section 202 thus provides additional sealing force when a pressure or force pushes the sealing member 100 towards the outside of the cervix 102. This may be the case, for example, when a pressure within the uterus 104 is increased as a result of a medical procedure conducted therein. Those skilled in the art will understand that the tapered section 202 is shaped to conform to a shape of the opening 208 and that this shape may be modified to suit the shapes of openings to any other hollow organs which are to be sealed.

As described above, in any of the exemplary devices according to the embodiments of the invention, suction may be applied throughout the duration of the procedure or at any times during the procedure during which it is desired to enhance the sealing of the hollow organ accessed. For example, suction may be initially applied to draw tissue surrounding the opening to the hollow organ against the sealing member 100 and subsequently discontinued with the tissue being kept in sealing contact with the sealing member 100 by the natural forces exerted by the tissue as well as by a residual vacuum remaining in the vacuum channel 114 and the vacuum line 115. Typically, the residual vacuum will maintain a desired seal unless a vacuum leak exists in the system. One advantage of maintaining continuously active suction is that any fluid leaking past the opening of the organ, for example through the cervix 102, will be removed through the suction holes 112, and the associated vacuum lines. In addition, the seal will be maintained even if one or more small vacuum leaks are present.

In the exemplary embodiments shown in FIGS. 1 and 2, the sealing member 100 is inserted into the cervix 102 with the suction apparatus off, to avoid interfering with and complicating the insertion of the elongated body 106 to the operative position. After the cervical sealing member 100 has been correctly positioned, the suction source 120 is activated to apply a vacuum between the inner walls of the cervix 102 and the outer surface of the sealing member 100 via the suction holes 112. The amount of suction provided may be varied depending on the size of the cervix 102 relative to the sealing member 100, and on the type of procedure to be carried out.

When there is no longer a need for the barrier provided by the sealing member 100, the source of vacuum 120 is deactivated and any residual vacuum in the system 101, 200 is released. For example, after an ablation procedure has been completed and the ablating fluid has been drained from the uterus 104, the vacuum source 120 is deactivated, pressure is allowed into the vacuum channel 114 to deplete any residual vacuum and the elongated body 106 is removed from the cervix 102. The shaft 108 is then manipulated by the operating professional remove the device employing, for example, a handle or other aid to manipulating the elongated body 106 which may optionally be included at the proximal end of the shaft 108.

The present invention was described with reference to specific exemplary embodiments. Those skilled in the art will understand that changes may be made in details, particularly in matters of shape, size, material and arrangement of parts. Accordingly, various modifications and changes may be made to the embodiments. For example, the exemplary devices described may be used to provide a fluid seal to openings of bodily cavities or hollow organs other than the cervix. The specifications and drawings are, therefore, to be regarded in an illustrative rather than a restrictive sense.

What is claimed is:

1. A method for accessing the uterus, comprising:
    inserting an elongated member through the cervix into the uterus so that a distal port of a working channel of the elongated member is open to the uterus while a proximal port of the working channel is open to the proximal side of the cervix, an outer diameter of a sealing portion of the elongated member sealingly engaging an inner wall of the cervix;
    applying suction to a vacuum channel of the elongated member to apply a negative fluid pressure to increase a sealing force applied by the sealing portion on the inner wall of the cervix via a plurality of suction holes extending through an outer wall of the sealing portion, the suction holes being arranged circumferentially around the sealing portion; and
    accessing the uterus such that an instrument is insertable into the uterus via the working channel.

\* \* \* \* \*